United States Patent
Brown et al.

(10) Patent No.: US 11,857,760 B2
(45) Date of Patent: *Jan. 2, 2024

(54) FLUID SENSOR

(71) Applicant: Honeywell International Inc., Charlotte, NC (US)

(72) Inventors: Andy Walker Brown, Richardson, TX (US); Adam D. McBrady, Dallas, TX (US)

(73) Assignee: Honeywell International Inc., Charlotte, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/052,166

(22) Filed: Nov. 2, 2022

(65) Prior Publication Data

US 2023/0158232 A1 May 25, 2023

Related U.S. Application Data

(63) Continuation of application No. 16/409,496, filed on May 10, 2019, now Pat. No. 11,517,670.

(51) Int. Cl.
*A61M 5/168* (2006.01)
*A61M 5/36* (2006.01)
(Continued)

(52) U.S. Cl.
CPC ........ *A61M 5/16854* (2013.01); *A61M 5/365* (2013.01); *A61M 39/08* (2013.01);
(Continued)

(58) Field of Classification Search
CPC .............. A61M 5/16854; A61M 5/365; A61M 2005/16863; A61M 2205/332;
(Continued)

(56) References Cited

U.S. PATENT DOCUMENTS

| | | | |
|---|---|---|---|
| 4,722,224 A | | 2/1988 | Scheller et al. |
| 5,039,279 A | * | 8/1991 | Natwick ........... A61M 5/14228 |
| | | | 417/474 |

(Continued)

FOREIGN PATENT DOCUMENTS

| | | |
|---|---|---|
| CN | 204092729 U | 1/2015 |
| JP | 2002-333434 | 11/2002 |

OTHER PUBLICATIONS

Advisory Action (PTOL-303) dated Jan. 13, 2023 for U.S. Appl. No. 16/370,099.

(Continued)

*Primary Examiner* — Kevin C Sirmons
*Assistant Examiner* — Avery Smale
(74) *Attorney, Agent, or Firm* — Alston & Bird LLP

(57) ABSTRACT

A fluid sensing apparatus and method for detecting pressure and a presence of a bubble within a fluid tube. The fluid sensing apparatus comprises a housing configured to receive a portion of the fluid tube and to house a pressure sensor and an ultrasonic transmitter. The pressure sensor is positioned adjacent the fluid tube and is configured to receive a pressure sensor signal, which correlates to a detected pressure differential within the fluid tube. A controller transmits a drive signal to the ultrasonic transmitter, which emits ultrasonic waves through a portion of the fluid tube and to the pressure sensor. The pressure sensor receives both the ultrasonic waves and the pressure sensor signal, and subsequently transmits an output signal to the controller. In a presence of the detected pressure differential or the bubble within the fluid tube, the output signal will exhibit a DC shift or a distortion of signal characteristics of the output signal, respectively.

20 Claims, 8 Drawing Sheets

(51) Int. Cl.
  *A61M 39/08* (2006.01)
  *G01N 29/22* (2006.01)
  *G01N 29/02* (2006.01)
(52) U.S. Cl.
  CPC ........... *G01N 29/02* (2013.01); *G01N 29/222* (2013.01); *A61M 2005/16863* (2013.01); *A61M 2205/332* (2013.01); *A61M 2205/3331* (2013.01)
(58) Field of Classification Search
  CPC ...... A61M 2205/3331; A61M 5/16831; A61M 2005/16868; A61M 2005/16872; A61M 5/36; A61M 2205/058; A61M 2205/3375; G01N 2291/02433; G01N 29/02; G01N 29/222; G01N 29/036
  See application file for complete search history.

(56) References Cited

U.S. PATENT DOCUMENTS

| | | | |
|---|---|---|---|
| 5,116,203 | A | 5/1992 | Natwick et al. |
| 5,661,245 | A | 8/1997 | Svoboda et al. |
| 7,661,294 | B2 | 2/2010 | Dam |
| 8,286,505 | B2 | 10/2012 | Wade |
| 8,770,010 | B1 | 7/2014 | Shapiro |
| 10,046,112 | B2 | 8/2018 | Oruklu et al. |
| 11,517,670 | B2 | 12/2022 | Brown et al. |
| 2002/0104370 | A1 | 8/2002 | Steger et al. |
| 2005/0145009 | A1 | 7/2005 | Vanderveen et al. |
| 2005/0212869 | A1 | 9/2005 | Ellson et al. |
| 2008/0066557 | A1 | 3/2008 | Yoshida |
| 2011/0130741 | A1 | 6/2011 | Miles et al. |
| 2011/0152642 | A1 | 6/2011 | Robinson |
| 2013/0296823 | A1 | 11/2013 | Melker et al. |
| 2015/0153262 | A1 | 6/2015 | Hies et al. |
| 2015/0224254 | A1* | 8/2015 | Sullivan ............ A61M 5/14228 604/151 |
| 2016/0045400 | A1 | 2/2016 | Hudson |
| 2018/0306559 | A1 | 10/2018 | Eberhart |
| 2018/0306659 | A1 | 10/2018 | Wade et al. |
| 2018/0306660 | A1 | 10/2018 | Wade et al. |

OTHER PUBLICATIONS

EP Office Action dated Nov. 19, 2021 for EP Application No. 20165405, 3 page(s).
European Search Report dated Jul 2, 2020 for EP Application No. 20165405, 8 page(s).
Examiner Interview Summary Record (PTOL-413) dated Oct. 21, 2021 for U.S. Appl. No. 16/409,496.
Final Office Action dated Oct. 25, 2022 for U.S. Appl. No. 16/370,099.
Final Rejection dated Apr. 27, 2021 for U.S. Appl. No. 16/409,496.
Non-Final Office Action dated Apr. 11, 2022 for U.S. Appl. No. 16/370,099.
Non-Final Rejection dated Jan. 27, 2022 for U.S. Appl. No. 16/409,496.
Non-Final Rejection dated Jul. 15, 2021 for U.S. Appl. No. 16/409,496.
Non-Final Rejection dated Nov. 23, 2020 for U.S. Appl. No. 16/409,496.
Notice of Allowance and Fees Due (PTOL-85) dated Aug. 3, 2022 for U.S. Appl. No. 16/409,496.
Office Action Appendix dated Oct. 21, 2021 for U.S. Appl. No. 16/409,496.
U.S. Patent Application filed Mar. 29, 2019 for U.S. Appl. No. 16/370,099.
Andy Walker Brown et al., U.S. Appl. No. 18/052,166 for "Fluid Sensor", filed Nov. 2, 2022.
Non-Final Rejection dated Feb. 10, 2023 for U.S. Appl. No. 16/370,099.
Notice of Allowance and Fees Due (PTOL-85) dated Jul. 5, 2023 for U.S. Appl. No. 16/370,099, 9 page(s).
Notice of Allowance and Fees Due (PTOL-85) dated Aug. 17, 2023 for U.S. Appl. No. 16/370,099, 6 page(s).

* cited by examiner

FLUID SENSOR

CROSS-REFERENCE TO RELATED APPLICATIONS

This application is a continuation of U.S. Non-Provisional application Ser. No. 16/409,496, entitled "FLUID SENSOR" and filed on May 10, 2019, which is incorporated herein by reference in its entirety.

BACKGROUND

Fluid sensors are used today to characterize fluids in a wide variety of applications including, for example, medical applications. In particular, fluid sensors may be incorporated as components of safety measures associated with intravenous infusions, a treatment measure in the daily routine of modern hospitals. Intravenous infusions utilize infusion pumps to administer fluids such as nutrients, blood, and medication intravenously to patients in controlled amounts.

Accordingly, a need exists for improved sensors characterized by a low error rate and minimized footprint.

BRIEF SUMMARY

Various embodiments relate to a fluid sensor contained within a singular housing that is configured to detect pressure changes and to detect the presence of air bubbles in-line while minimizing both the error rate and the footprint of the sensor. Various embodiments are directed to a fluid sensor comprising an ultrasonic transmitter configured to emit ultrasonic signals through an emitting face, a pressure sensor configured to detect pressure changes through a receiving face and to receive ultrasonic signals from the ultrasonic transmitter, and a controller, wherein the emitting face of the ultrasonic transmitter may be spaced apart from the receiving face of the pressure sensor to collectively define a gap configured to receive a fluid delivery conduit therein, and wherein the controller is configured to detect the presence of at least one bubble flowing through a fluid delivery conduit positioned within the gap based at least in part on a frequency-based analysis of a pressure sensor output signal. The emitting face of the ultrasonic transmitter and the receiving face of the pressure sensor may collectively define a gap. The gap may be adjustable to compress a fluid delivery conduit within the gap and between the emitting face of the ultrasonic transmitter and the receiving face of the pressure sensor. The pressure sensor may be configured to detect a change in pressure within a fluid delivery conduit compressed within the gap and monitor ultrasonic signals received from the ultrasonic transmitter to detect bubbles flowing through the fluid delivery conduit compressed within the gap.

In various embodiments, the fluid sensor may comprise an ultrasonic transmitter configured to emit ultrasonic signals through an emitting face and a pressure sensor configured to detect pressure changes through a receiving face, wherein the emitting face of the ultrasonic transmitter is spaced apart from the receiving face of the pressure sensor to collectively define a gap configured to receive a fluid delivery conduit therein; and wherein the pressure sensor is configured to detect a change in pressure within a fluid delivery conduit positioned within the gap; and receive ultrasonic signals from the ultrasonic transmitter to detect bubbles flowing through the fluid delivery conduit positioned within the gap. In various embodiments, the fluid sensor may further comprise a housing, wherein the housing comprises an exterior housing portion and an interior housing portion, and wherein the ultrasonic transmitter and the pressure sensor are enclosed within the interior housing portion. In various embodiments, the housing may be blow-molded, injection molded, or manufactured by any other suitable means. In various embodiments, the interior housing portion further defines a channel configured to secure at least a portion of the fluid delivery conduit within the interior portion of the housing and wherein at least a portion of the channel defines the gap. Further, in various embodiments, a portion of the fluid delivery conduit positioned within the gap is compressed such that the at least substantially all of the receiving face of the pressure sensor is engaged by a portion of the fluid delivery conduit.

In various embodiments, the pressure sensor may comprise a pressure sensing element mounted to a substrate and a force transmitting member positioned adjacent to the pressure sensing element, wherein the force transmitting member transmits a force applied to the front side of the force transmitting member to the front side of the pressure sensing element. In various embodiments, the force transmitting member may be a gel.

In various embodiments, a controller may be configured for wireless communication of an output signal. Further, in various embodiments, the ultrasonic transmitter is configured to receive a drive signal from a controller, wherein the drive signal comprises at least one of an AC component or a DC component. In various embodiments the ultrasonic transmitter may comprise a piezoelectric ultrasonic transducer, and may further comprise an ultrasonic generator. In various embodiments, the fluid sensor may be configured to detect a change in pressure within a fluid delivery conduit based at least in part on a detected shift in a received signal. Further, in various embodiments, the controller may be configured to construct transformed data by performing a Fast Fourier Transform of the pressure sensor output signal, wherein the transformed data is indicative of the strength of the pressure sensor output signal across a frequency range. In various embodiments, the fluid sensor may configured to detect the presence of at least one bubble flowing through the fluid delivery conduit by measuring the detected change in the transformed data at a frequency that is at least substantially similar to a drive frequency of the ultrasonic transmitter. In various embodiments, the controller may be configured to construct transformed data by utilizing a bandpass filter centered at a frequency at least substantially similar to a drive frequency of the ultrasonic transmitter to selectively distinguish the pressure sensor output signal at the ultrasonic transmitter drive frequency from the noise present within the signal.

Various embodiments may be directed to a method of detecting occlusion and the presence of bubbles within a fluid delivery conduit, the method comprising: detecting a change in pressure within a fluid delivery conduit based at least in part on a detected shift in a received signal and detecting an air bubble within the fluid delivery conduit based at least in part on a detected change in transformed data indicative of at least a portion of the pressure sensor output signal, wherein a signal output by the pressure sensor comprises both an AC and a DC component. In various embodiments, the method may further comprise emitting ultrasonic signals from an ultrasonic transmitter, through the fluid delivery conduit, and to a pressure sensor aligned with the ultrasonic transmitter on an opposite side of the fluid delivery conduit and configured to receive the ultrasonic signals emitted from the ultrasonic transducer. In various embodiments, the signal emitted from the ultrasonic transmitter comprises an AC signal. In various embodiments, a DC shift in the pressure sensor's output signal corresponds to a change in pressure within the fluid delivery conduit. In various embodiments, the method may further comprise communicating the pressure sensor's output signal to one or more external devices. In various embodiments, a controller is configured for wireless communication of an output signal.

BRIEF DESCRIPTION OF THE DRAWINGS

Reference will now be made to the accompanying drawings, which are not necessarily drawn to scale, and wherein.

DETAILED DESCRIPTION

Figure 1:
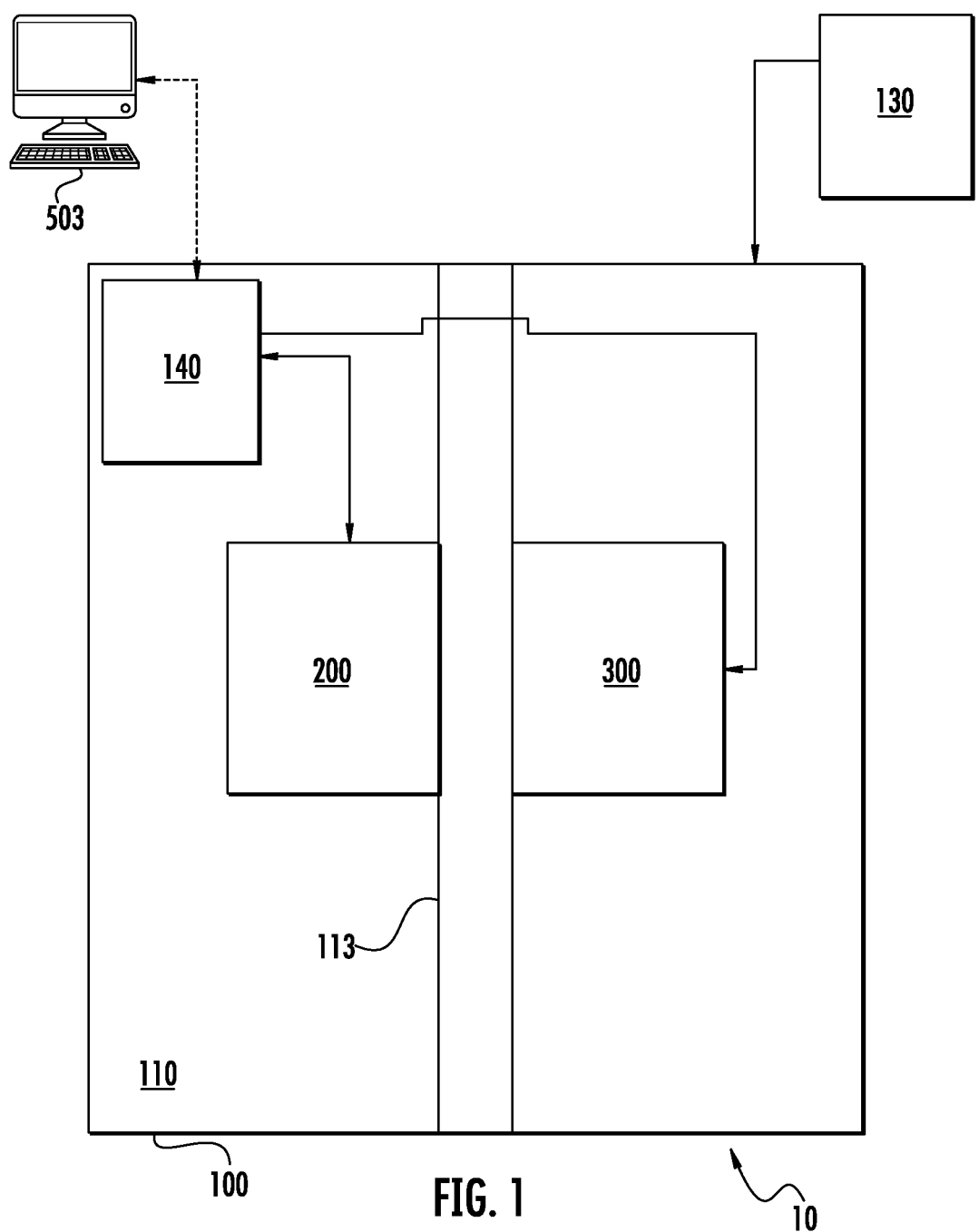
FIG. 1 schematically illustrates communication among various components in accordance with some embodiments discussed herein.

The present disclosure more fully describes various embodiments with reference to the accompanying drawings. It should be understood that some, but not all embodiments are shown and described herein. Indeed, the embodiments may take many different forms, and accordingly this disclosure should not be construed as limited to the embodiments set forth herein. Rather, these embodiments are provided so that this disclosure will satisfy applicable legal requirements. Like numbers refer to like elements throughout.

Overview

Described herein is a fluid sensor configured to characterize and monitor the fluid within a fluid delivery conduit. In an example implementation, a fluid sensor as discussed herein may be utilized to monitor fluid in tubes utilized in a medical environment (e.g., blood flow tubes, fluid delivery tubes, and/or the like). The fluid sensor discussed herein may be configured to utilize non-invasive ultrasonic technology to detect the presence of air bubbles within a tube. Such configurations are capable of point and continuous sensing, able to detect small bubbles, efficient with respect to power consumption, durable, compatible with a variety of tubing materials, and less sensitive to particle accumulation. The fluid sensor of certain embodiments described herein exhibits the aforementioned advantages, while further comprising components that enable both low-cost production and a decreased sensor footprint. Critically, a minimized sensor footprint may, in certain applications (e.g., medical infusion), enable monitoring at a point of entry into a patient's body, which may result in a more accurate dosage delivery.

As described herein, the fluid sensor may detect pressure changes within the tube, which may be caused by, for example, an occlusion causing a decrease or increase in fluid pressure within the tube due to a blockage within the tube (which may be detected in light of either an increase or a decrease in pressure within the tube depending on whether the blockage is upstream or downstream from the sensor). The sensor may also detect bubbles, which as described herein encompass a volume of gas having a surface defined as an interface between the gaseous fluid (within the interior of the bubble) and a liquid fluid (at least partially surrounding the exterior of the bubble).

A fluid sensor in accordance with various embodiments may be configured as described in co-pending U.S. application Ser. No. 16/370,099, filed Mar. 29, 2019, which is incorporated herein by reference in its entirety. Fluid sensors as discussed herein comprise both a pressure sensor and an ultrasonic transmitter, and characterize the flow in a tube positioned between the pressure sensor and the ultrasonic transmitter by measuring the in-line fluid pressure and detecting in-line air bubbles. The fluid sensor further comprises a housing configured receive at least a portion of a fluid delivery conduit, and to house the pressure sensor and the ultrasonic transmitter. Within the housing, the pressure sensor is positioned on one side of the fluid delivery conduit and the ultrasonic transmitter is positioned across from the pressure sensor on an opposite of the tubing; the two elements are aligned so as to face one another such that the ultrasonic transmitter emits ultrasonic signals through the fluid delivery conduit and into the face of the pressure sensor. To ensure the accuracy of the pressure sensor output, the portion of the fluid delivery conduit enclosed within the housing may be compressed such that at least a portion of the face of the pressure sensor is in contact with the wall of the fluid delivery conduit. In particular embodiments, at least substantially all of the face of the pressure sensor is in contact with the wall of the fluid delivery conduit. Alternatively, the pressure sensor and the ultrasonic transmitter may be positioned adjacent to one another on the same side of the fluid delivery conduit. The two elements may be aligned so as to face into the fluid delivery conduit in substantially the same direction such that the ultrasonic transmitter may emit ultrasonic signals through the fluid delivery conduit and into a reflector element positioned to reflect the emitted signals back through the fluid delivery conduit and into the face of the pressure sensor.

The pressure sensor may comprise a pressure sensing element, which may, for example, be embedded in a coupling gel or some other force transmitting member such that low frequency, pressure-related signals detected as occurring within the tube (e.g., caused by occlusion) are sensed by the pressure sensing element as the gel transmits the signal from the tube (e.g., from the surface of the tube in contact with a surface of the force transmitting member). Such a configuration allows for the ultrasonic transmitter to emit high frequency signals through the tube and through the gel before reaching the pressure sensing element, thereby enabling the sensor's bubble detection functionality. The fluid sensor of certain embodiments detects AC and DC signal components of a signal transmitted from the ultrasonic transmitting member to characterize the in-line flow: the DC component is utilized to detect changes in pressure within the tube (e.g., which may be caused by occlusion), while the AC component is utilized for the bubble detection. In various embodiments, the fluid sensor may perform a Fast Fourier Transform (FFT) to convert the pressure sensor output signal into the frequency domain. The fluid sensor of certain embodiments determines the strength of the output signal at the ultrasonic transmitter frequency and, understanding the characteristics of a signal during both a baseline fluid-in-tube condition and an air-in-tube condition, correlates a more pronounced signal at a frequency of interest (e.g., the drive frequency) to the presence of an in-line bubble. As designed, the fluid sensor effectively reduces error rate by utilizing a dual sensor configuration (i.e. the simultaneous AC and DC signal components) to be used to compensate for inaccurate variations in the sensor's reading resulting from drifts in the acoustic baseline due to unwarranted changes in contact force (e.g., tubing deformation, temperature change, fluid pressure, etc.).

Housing/Sensor Construction

Figure 2:
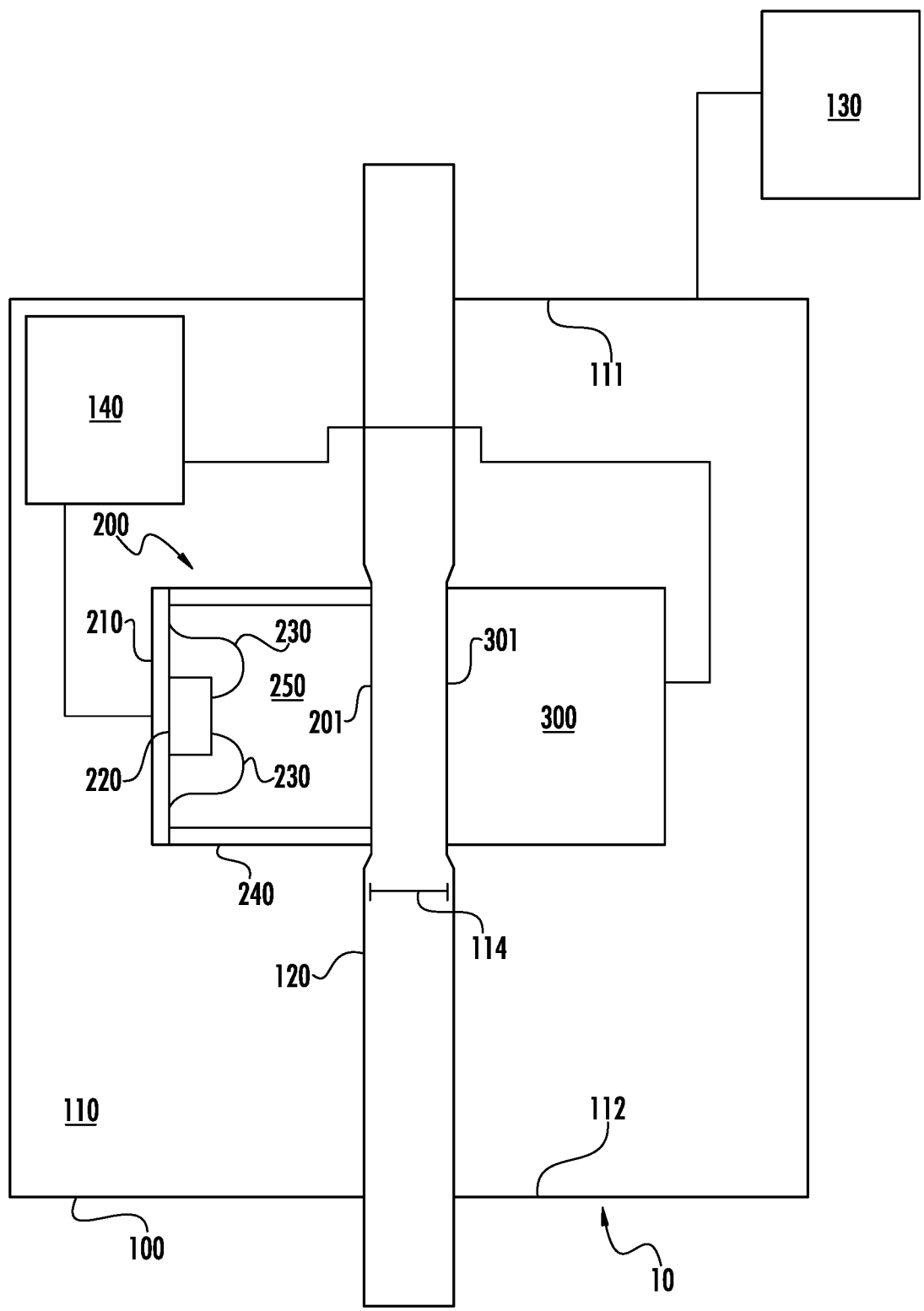
FIG. 2 schematically illustrates an exemplary sensor in accordance with various embodiments.
Figure 3:
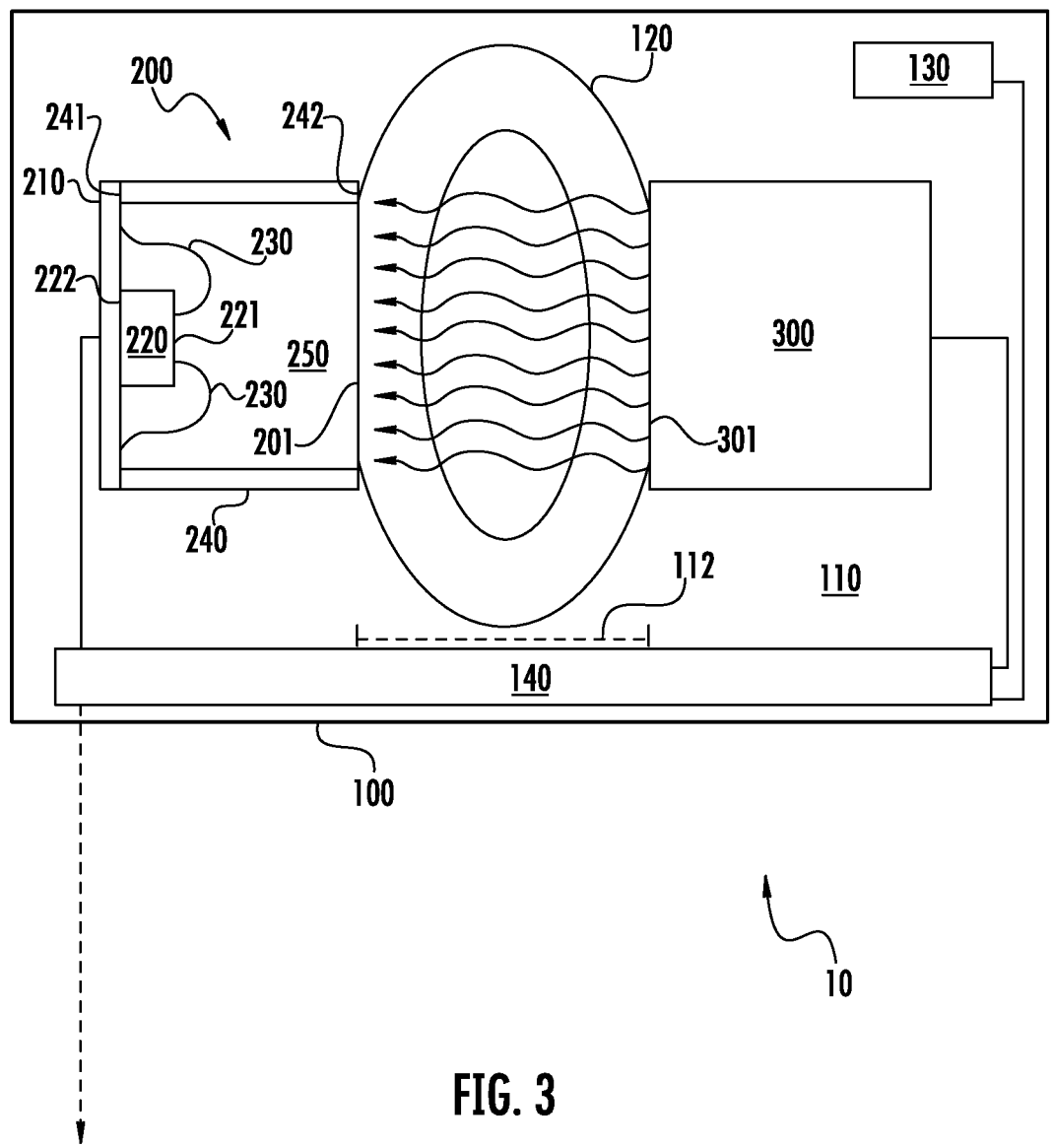
FIG. 3 illustrates a cross-sectional view of an exemplary apparatus as described herein without a bubble in the fluid delivery conduit.

As shown in FIGS. 1-3, the fluid sensor 10 comprises a housing 100. The housing 100 defines the exterior of the fluid sensor 10 and may have a height, length, and a width, wherein the length of the housing 100 is defined by the distance between a first end and a second end. As illustrated in FIG. 1, the housing may further comprise a channel 113 extending from the first end of the housing 100 to the second end and configured to receive and secure at least a portion of a fluid delivery conduit. Housing 100 may be configured to enclose both the pressure sensor 200 and the ultrasonic transmitter 300 within the interior portion of the housing. The pressure sensor 200 and the ultrasonic transmitter 300 are each coupled to an interior portion of the housing 110 and are spaced apart within the interior portion of the housing 110 to define a gap 114 between the two elements. In various embodiments, the width of the gap 114 may be substantially equal to the width of the channel 113 and may run parallel to (and/or coextensive with) at least a portion of the channel 113. The pressure sensor 200 and the ultrasonic transmitter 300 of the illustrated embodiment are aligned within the housing 100 so as to face one another; that is, the emitting face of the ultrasonic transmitter 301 should be facing toward the receiving face of the pressure sensor 201 such that high frequency waves generated by the ultrasonic transmitter 300 and emitted from the emitting face of the ultrasonic transmitter 301 travel towards the receiving face of the pressure sensor 201. In such an exemplary configuration, the pressure sensor 200 and the ultrasonic transmitter 300 may be arranged to face a direction perpendicular to the length of the channel 113, and may define at least a portion of the channel 113.

In various embodiments, the fluid delivery conduit may have a length, and a diameter, and may comprise an outer circumferential wall, an inner circumferential wall, and a wall thickness extending between the outer circumferential wall and the inner circumferential wall; and an interior channel within the inner wall configured to direct the flow of fluid from one location to a second location. The fluid delivery conduit may comprise a resilient material (e.g., a silicone material, a polyvinyl chloride material, and/or the like).

The housing 100 may be configured to receive at least a portion of a fluid delivery conduit 120 through the channel. A portion of fluid delivery conduit 120 may extend from a first end of the housing 111 to a second end of the housing 112. The fluid delivery conduit 120 may be positioned within the channel 113 such that it runs parallel to and intersects the gap 114. In such a configuration, at least a portion of the fluid delivery conduit 120 is between the pressure sensor 200 and the ultrasonic transmitter 300. In such an exemplary configuration, the pressure sensor 200 and the ultrasonic transmitter 300 may be arranged to face a direction perpendicular to the length of the fluid delivery conduit 120. Further, the pressure sensor 200 and the ultrasonic transmitter 300 may be centered at the same position along the length of the fluid delivery conduit such that the gap 114 between the two elements is substantially perpendicular to the length of the fluid delivery conduit.

As described above and as illustrated in FIGS. 2-4, at least a portion of the fluid delivery conduit 120 may be positioned between and adjacent to the pressure sensor 200 and the ultrasonic transmitter 300 such that when the ultrasonic transmitter 300 emits signals (e.g., high frequency ultrasonic signals) in the direction of the pressure sensor 200, the signals pass through a cross-section of the fluid delivery conduit 120. The housing 100 may be adjustably configured such that the width of the gap 114 between the pressure sensor 200 and the ultrasonic transmitter 300 may be smaller than the diameter of fluid delivery conduit 120, thereby causing a compression force to be applied to a portion of the outer wall of the fluid delivery conduit 120 secured within the gap 114. The compression force may be applied in a direction perpendicular to the length of the fluid delivery conduit 120 such that the outer wall of the fluid delivery conduit 120 is pressed against the receiving face of the pressure sensor 201. In such an exemplary configuration, the applied compression force may be sufficient to cause at least substantially all of the receiving face of the pressure sensor 201 to be engaged by the compressed outer wall of the fluid delivery conduit 120. In various embodiments, the compression force may be user-defined and/or dependent on one or more characteristics of the fluid delivery conduit 120 such as, for example, wall thickness, material type, outer diameter, inner diameter, and any other characteristic of the fluid delivery conduit 120. In various embodiments, the fluid sensor 10 may be further configured to monitor a compressive force applied to a portion of the fluid delivery conduit 120 positioned between the receiving face of the pressure sensor 201 and the ultrasonic transmitter 300 (e.g., using an ancillary pressure sensor). The measured compressive force applied to the portion of the fluid delivery conduit 120 may be utilized in certain embodiments to calibrate pressure sensor 200 readings of pressure within the fluid delivery conduit 120. In other embodiments, the fluid sensor 10 may be separately calibrated for pressure sensor 200 readings of pressure within the fluid delivery conduit 120.

In some embodiments, the fluid sensor 10 may be connected to a power supply 130 configured to receive power and power the fluid sensor. As non-limiting examples, the power supply 130 may comprise one or more batteries, one or more capacitors, one or more constant power supplies (e.g., a wall-outlet), and/or the like. In some embodiments, as shown in FIG. 2, the power supply 130 may comprise an external power supply positioned outside of the housing 100 and configured to deliver alternating or direct current power to the fluid sensor 10. Further, in some embodiments, as illustrated in FIG. 3, the power supply 130 may comprise an internal power supply, for example, one or more batteries, positioned within the housing 100.

Figure 4:
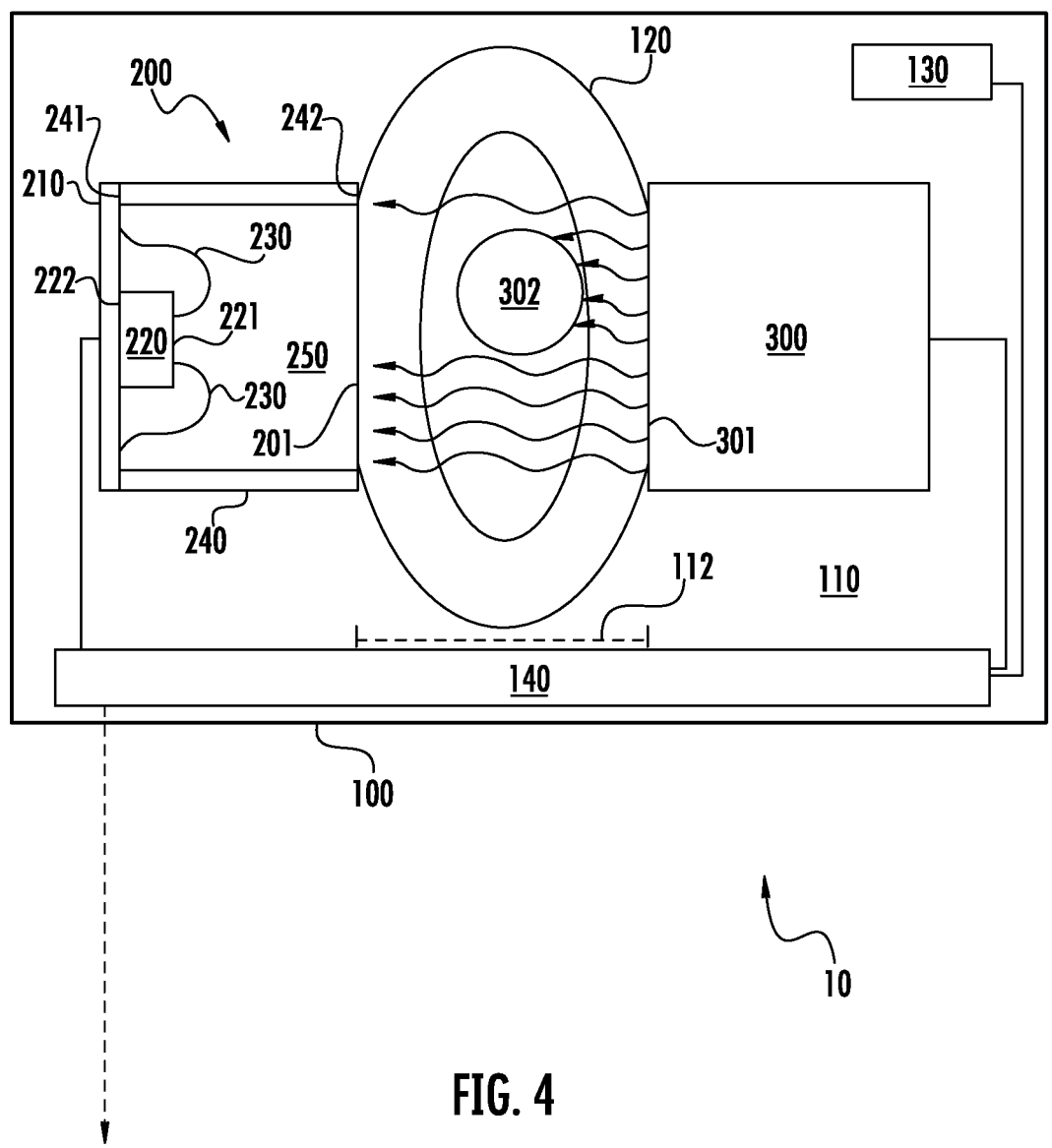
FIG. 4 illustrates a cross-sectional view of an exemplary apparatus as described herein with a bubble in the fluid delivery conduit.

In various embodiments, power may be supplied to controller 140 to enable distribution of power to the various components described herein. In some embodiments, each of the components of the fluid sensor 10 may be connected to controller 140 (e.g., for electronic communication), which may be configured to facilitate communication and functional control therebetween. In various embodiments, the controller 140 may comprise one or more of a processor, memory, a communication module, an on-board display 150, and signal analysis circuitry. For example, the controller 140 may comprise a driving circuit and a signal processing circuit. In various embodiments, the controller 140 may be configured to power the pressure sensor 200 and/or receive an output signal from the pressure sensor 200. In various embodiments, the controller 140 may be configured to power the ultrasonic transmitter 300 and/or transmit a drive signal to the ultrasonic transmitter 300. In various embodiments, as shown in FIGS. 3 and 4, the controller may be configured to transmit output signals out to external components via universal serial bus (USB) or any other wired connection. In various embodiments, an on-board display may be configured to display a variety of signals transmitted from or received by the controller 140, and/or the like. In various embodiments, the controller may be embodied as a single chip (e.g., a single integrated-circuit chip) configured to provide power signals to both the pressure sensor 200 and the ultrasonic transmitter 300, to receive and process the output signal from the pressure sensor 200, and/or to compensate for any detected changes in environmental factors such as, for example, temperature, flow, or pressure within the fluid delivery conduit 120. Such a configuration may be desirable to minimize production costs and reduce the physical footprint of the fluid sensor 10.

Figure 5:
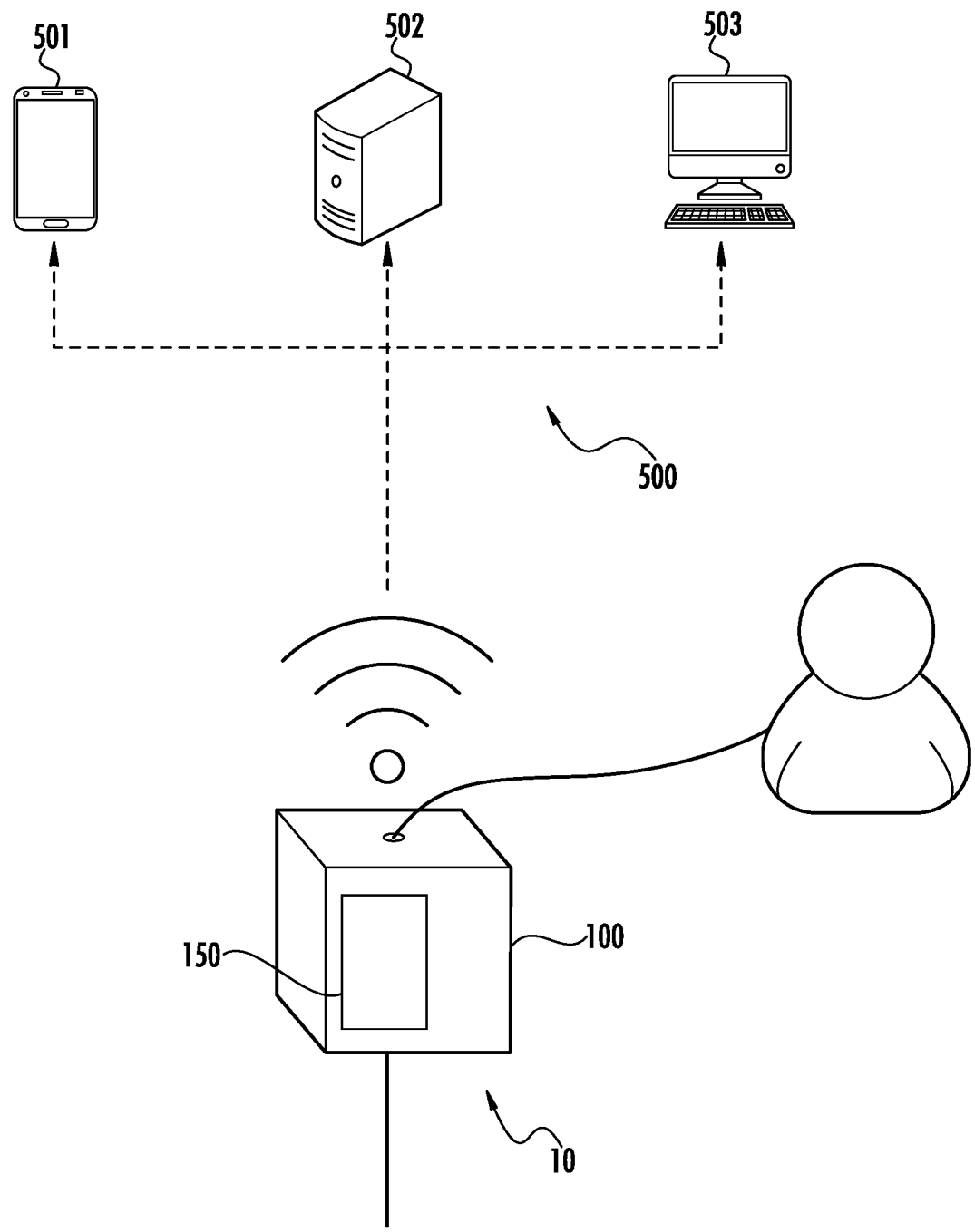
FIG. 5 illustrates data flows among components in accordance with some embodiments discussed herein.

As described above and as will be appreciated based on this disclosure, various embodiments may be configured in various forms including with portions of the fluid sensor 10 shown in FIG. 5 being remote from the apparatus. In various embodiments, all of the components necessary to characterize the flow through a fluid delivery conduit 120 may be integrated into a single housing 100. In various embodiments, the controller 140 may be configured to communicate with a variety of external devices via Bluetooth™ Bluetooth Low Energy (BTLE), Wi-Fi™, or any other wireless connection. As shown in FIG. 5, the controller may be configured so as to enable wireless communication within an Internet-of-Things (IoT) network 500 to a variety of wirelessly enabled devices (e.g., a user mobile device 501, a server 502, a computer 503, and/or the like).

In various embodiments, the controller 140 may comprise signal analysis circuitry, which may be configured to perform frequency based analysis of a pressure sensor output signal to determine whether a bubble is present within the fluid delivery conduit 120. For example, the signal analysis circuitry may receive the pressure sensor output signal and perform a Fast Fourier Transform (FFT) to observe a signal representation in the frequency domain. In various embodiments, the signal analysis circuitry may be configured to analyze the transformed data and further to detect a bubble in the fluid delivery conduit 120 based at least in part on, for example, one or more of the measured strength of the signal at the known ultrasonic transmitter drive frequency, a signal contrast ratio between a measured signal and a baseline fluid-in-tube condition to an in-line bubble, and a signal-to-noise ratio of the transformed data at the ultrasonic transmitter drive frequency. In various embodiments, the transformed data may indicate a distinguishably higher signal strength at the ultrasonic transmitter drive frequency during an air-in-tube condition compared to the signal strength at the ultrasonic transmitter drive frequency during a fluid-in-tube condition. In various embodiments, the measured signal strength value may vary based on, for example, one or more of fluid delivery conduit 120 size, fluid delivery conduit 120 material, ultrasonic signal strength, signal amplifier gain, and any other applicable parameter specific to the implemented embodiment. In various embodiments, an air-in-tube condition may be detected by comparing the signal-to-noise ratio of the transformed data in an air-in-tube condition to that of the transformed data in a fluid-in-tube condition at the ultrasonic transmitter drive frequency. For example, a high signal contrast ratio may be indicative of the presence of a bubble within the tube. In various embodiments, a signal contrast ratio of between 2 and 5 (e.g., 3) may be measured when comparing the aforementioned respective transformed data. As described herein, when the fluid sensor 10 detects a signal contrast ratio as described above at the ultrasonic transmitter drive frequency with a value of at least 1 kHz, the controller 140 may be configured to determine that a bubble is present in the fluid delivery conduit 120.

In various embodiments, the signal analysis circuitry may further comprise a bandpass filter configured to isolate one or more signals of interest within a particular band of frequencies. In various embodiments, the bandpass filter range may be centered at the drive frequency of the ultrasonic transmitter and may be configured to allow a range of frequencies between, for example, within 500 Hz above and/or below the drive frequency to be received (e.g., a 1 kHz band). In various embodiments, the bandpass filter may be used to selectively distinguish the signal at the ultrasonic transmitter drive frequency from the noise present within the signal. In certain embodiments, the bandpass filter may sufficiently isolate the drive frequency of the ultrasonic transmitter that characteristics of the output signal (e.g., in the time-domain) may be utilized to detect the presence of a bubble within the fluid delivery conduit. For example, signal amplitude, detected presence (or absence) of a signal at the drive frequency, and/or the like may be utilized to determine whether a bubble is present within the fluid delivery conduit. It should be understood that the bandpass filter may be embodied as hardware and/or software. In various embodiments, the signal analysis circuitry may further comprise a signal amplifier configured to increase the strength of the pressure sensor output signal. In various embodiments, the signal amplifier may be used to strengthen the pressure sensor output signal so as to ensure that the signal at the ultrasonic transmitter drive frequency may be detected by the signal analysis circuitry.

The use of the term "circuitry" as used herein with respect to components of the fluid sensor 10 therefore includes particular hardware configured to perform the functions associated with respective circuitry described herein. Of course, while the term "circuitry" should be understood broadly to include hardware, in some embodiments, circuitry may also include software for configuring the hardware. For example, in some embodiments, "circuitry" may include processing circuitry, storage media, network interfaces, input-output devices, and other components. In some embodiments, other elements of the controller 140 may provide or supplement the functionality of particular circuitry. For example, the processor may provide processing functionality, memory may provide storage functionality, and communication module may provide network interface functionality, among other features.

Pressure Sensor

As shown in FIGS. 1-4, the fluid sensor 10 may comprise a pressure sensor 200. The pressure sensor may be embodied as a pressure sensor such as that described in U.S. Patent Publ. No. 2018/0306659, which is incorporated herein by reference in its entirety. In various embodiments, the pressure sensor 200 may comprise a printed circuit board 210, a pressure sensing element 220, a sidewall 240, and a force transmitting member 250. As described above, the pressure sensor may be positioned within the housing 100 and coupled to an interior portion of the housing 100. The pressure sensor 200 may further comprise a receiving face 201, which may be, for example, either a flat, convex, or concave surface. The pressure sensor may be arranged such that the receiving face 201 is aligned with and facing the emitting face of the ultrasonic transmitter 301. The receiving face of the pressure sensor 201 may be spaced apart from the emitting face of the ultrasonic transmitter 301 at a distance defining the gap 114.

The substrate 210 of the pressure sensor 200 may be any type of printed control board (PCB), a ceramic substrate, or other suitable substrate configuration. In some embodiments, the substrate 210 may be a thick film printed ceramic board, however other circuit board configurations may be utilized in other embodiments. In one example, the substrate 210 may be made, at least in part, of FR 4 laminate and/or other material. In various embodiments, the substrate 210 may have one or more electronic components thereon and/or pads for connecting to electronic components of a device in which the pressure sensor 200 may be inserted or with which the pressure sensor 200 may be used. In one example, the substrate 210 may include an application specific integrated circuit (ASIC) that may be attached to the substrate 210. Such an ASIC may be electrically connected to the substrate 210 via wire bonds, bump bonds, electrical terminals, and/or any other suitable electrical connections. Additionally or alternatively, the substrate 210 may include one or more conductive pads for engaging circuitry and/or electronic components in communication with a remote processor or the like.

Further, the substrate 210 may include one or more processing electronics and/or compensation circuitry (e.g., which may or may not include an ASIC). Such processing electronics may be electrically connected to terminals of the pressure sensing element 220, an ASIC (if present), and/or electrical terminals to process electrical signals from the pressure sensing element 220 and/or to transfer outputs from the pressure sensing element 220 to electronic components of one or more devices used in conjunction with the pressure sensor 200. In some instances, the substrate 210 may include circuitry that may be configured to format one or more output signals provided by the pressure sensing element 220 into a particular output format. For example, circuitry of the substrate 210 (e.g., circuitry on one or more of sides of the substrate 210) may be configured to format the output signal provided by pressure sensing element 220 into a ratio-metric output format, a current format, a digital output format and/or any other suitable format. In some cases, the circuitry of the substrate 210 may be configured to regulate an output voltage. Circuitry on the substrate 210 for providing a ratio-metric (or other) output may include traces and/or other circuitry that may serve as a conduit to test pads, and/or for providing the ratio-metric (or other) output to one or more electrical terminals facilitating electrical connections with electronic components of one or more devices used with the pressure sensor 200.

The pressure sensing element 220 of the pressure sensor 200 may be configured in any manner and may have a first side 221 (e.g., a front side) and a second side 222 (e.g., a back side). In some cases, the pressure sensing element 220 may include a micro-machined pressure sense die that includes a sense diaphragm. In various embodiments, the pressure sensing element 220 may be back-side mounted on the substrate 210 with the second side of the pressure sensing element 222 facing the substrate 210 and may be configured to perform top-side sensing (e.g. sensing with the first side of the pressure sensing element 221). In a pressure sensing element 220 configuration, the top-side sensing may be when a sensed media either directly or indirectly (e.g., through the force transmitting member 250 or other intermediary) interacts with a top side of the pressure sensing element 221. Back-side mounting the pressure sensing element 220 to the substrate 210 may facilitate creating a robust pressure sensor 200 because any sensed media acting on the pressure sensing element 220 may act to push the pressure sensing element 220 against the substrate 210. Although the pressure sensing element 220 may be described herein as being back-side mounted to the substrate 210, it is contemplated that the pressure sensing element 220 may be mounted relative to the substrate 210 in one or more other configurations. For example, the pressure sensing element 220 may be front side mounted or mounted in any other suitable manner. Further, the pressure sensing element 220 may be electrically connected to the substrate 210 in one or more manners. In various embodiments, wire bonds 230 may be utilized to electrically connect the pressure sensing element 220 to the substrate 210. The wire bonds 230 may have a first end connected to a bond pad of the pressure sensing element 220 and another end connected to a bond pad of the substrate 210. Additionally or alternatively, the pressure sensing element 220 may be electrically connected to the substrate 210 via bump bonds and/or in any other suitable manner.

The sidewall 240 of the pressure sensor 200 may extend from a first end 241 to a second end 242. In various embodiments, the sidewall 240 may entirely or at least partially circumferentially surround and/or enclose the pressure sensing element 220, wire bonds 230, bond pads, the force transmitting member 250, and/or other components of the pressure sensor 200. The sidewall 240 may have a cross-section substantially circular or any other suitable shape. The sidewall 240 may be connected to the substrate 210 such that the second end of the sidewall 242 may face the substrate 210 and the first end of sidewall 240 may be spaced away from the substrate 210. In some cases, the sidewall 240 may be attached to at least a portion of the substrate 210 to provide additional structural integrity to the pressure sensor 200. The first end of the sidewall 241 may be positioned substantially adjacent the receiving face of the pressure sensor 201 and may at least partially define an opening from the first end of the sidewall 241 to the pressure sensing element 220 (e.g., a reservoir defined by the sidewall 240). The sidewall 240 may be made from any type of material. In one example, the sidewall 240 may be made from a plastic, a metal, a ceramic and/or any other suitable material.

In various embodiments, the force transmitting member 250 of the pressure sensor 200 may comprise a first end and a second end, wherein the first end may be configured to entirely engage a portion of the outer wall of the fluid delivery conduit 120 positioned within the gap 114 and the second end may be configured to interact with the pressure sensing element 220. The force transmitting member 250 may fill or at least partially fill the opening and/or reservoir of the sidewall 240. In various embodiments, the force transmitting member 250 may be configured to facilitate transferring a force interacting with the first end of the force transmitting member 250 to the pressure sensing element 220. In such an exemplary configuration, the force experienced by the pressure sensing element 220 may arise due to a change in pressure within the fluid delivery conduit 120 caused by a pressure change event (e.g., occlusion) and may result in a shift in the DC signal produced by the pressure sensor 200.

The force transmitting member 250 may be formed from one or more layers of material. For example, the force transmitting member 250 may be formed from one layer of material, two layers of material, three layers of material, four layers of material, five layers of material, or other number of layers of material. The force transmitting member 250 may be made from any suitable material. In various embodiments, the force transmitting member 250 may comprise a dielectric material, a non-compressible material, a biocompatible material, colored material, non-colored material, and/or one or more other types of material. Further, in various embodiments the force transmitting member 250 may comprise a gel (e.g., a fluoro-silicone gel), a resilient material such as a cured silicone rubber or silicone elastomer, a cured liquid silicone rubber, an oil and/or any other suitable material. In various embodiments, the force transmitting member 250 may include a biocompatible material such as, for example, a cured silicone elastomer, that is medically safe to directly contact medicines or the like that are to be provided to a patient. In various embodiments wherein the force transmitting member 250 comprises a gel, the pressure sensor may further comprise a membrane configured to cover the entirety of the opening at the first end of the sidewall 240 so as to contain the gel within the cavity.

In various embodiments, the pressure sensor 200 may be electronically connected to the controller 140 such that the controller 140 transmits a power signal to the pressure sensor 200. In various embodiments, the pressure sensor 200 may be powered at a voltage of between 1.5 volts and 15 volts (e.g., 5 volts). The pressure sensor 200 may be configured to, upon sensing both a pressure sensor signal created by a pressure differential within the fluid delivery conduit 120 and a high frequency ultrasonic waves from the ultrasonic transmitter 300, transmit an output signal comprising both an AC component and a DC component to the controller 140.

Ultrasonic Transmitter

As shown in FIGS. 1-4, the fluid sensor 10 may comprise an ultrasonic transmitter 300, which, in various embodiments, may be coupled to the interior portion of the housing 110. The ultrasonic transmitter 300 may define an emitting face 301 and may be arranged such that the emitting face 301 is aligned with and facing the receiving face of the pressure sensor 201. The emitting face of the ultrasonic transmitter 301 may be spaced apart from the receiving face of the pressure sensor 201 at a distance defining the gap 114. As illustrated in FIGS. 3 and 4, the ultrasonic transmitter 300 may be configured to generate and emit an ultrasonic signal in a direction substantially perpendicular to the emitting face 301, through the fluid delivery conduit 120, and towards the receiving face of the pressure sensor 201 such that the signal may be detected by the pressure sensing element 220.

As is generally understood in the art, the ultrasonic transmitter 300 may, in various embodiments, comprise an ultrasonic generator and an ultrasonic transducer. In various embodiments, the ultrasonic transducer may be, for example, a piezoelectric ultrasonic transducer. A piezoelectric ultrasonic transducer may comprise, for example, a ceramic disc (e.g., PIC255) and wrap-around electrodes configured to establish an electrical connection at a favorable position within the transducer assembly. In various embodiments, the ultrasonic transducer may have a diameter of between 2 mm and 15 mm (e.g., between 5 mm and 10 mm) and may have a thickness of between 0.5 mm and 4 mm (e.g., between 1 mm and 2 mm). In various embodiments, the ultrasonic transmitter 300 may be tuned for optimal interaction with and response by the pressure sensing element 220.

In various embodiments, the ultrasonic transmitter 300 may be electronically connected to the controller 140 such that the ultrasonic transmitter 300 may be powered by the controller 140. The controller 140 may be configured to further supply the ultrasonic transmitter 300 with a fixed frequency drive signal generally in the form of an oscillating signal, such as a sine-wave, square wave, triangular wave, sawtooth wave, and/or the like. However, it should be understood that other signal shapes may be provided as discussed herein. In various embodiments, the drive signal sent from the controller 140 to the ultrasonic transmitter 300 may manifest as a voltage centered between 1.5 volts and 100 volts (e.g., 5 volts). The ultrasonic transmitter 300 may be configured to receive the signal from the controller 140 and emit high frequency ultrasonic waves through the emitting face 301 and across a portion of the fluid delivery conduit 120 such that it may be received by the pressure sensor 200.

Pressure Sensing

As described herein, the fluid sensor 10 may be configured to detect occlusion (or other fluid pressure-changing events) within a fluid delivery conduit 120 by detecting a change in pressure within the fluid delivery conduit 120. As shown in FIGS. 2-4, the pressure sensor 200 of the fluid sensor 10 may be located within the interior of the housing 110 and arranged such that the receiving face of the pressure sensor 201 is at least substantially parallel and adjacent to a length of the channel 113 configured to receive and secure at least a portion of the fluid delivery conduit 120. Similarly, the emitting face of the ultrasonic transmitter 301 may be positioned at least substantially parallel to both the receiving face of the pressure sensor 201 and the length of the channel 113 configured to receive and secure at least a portion of the fluid delivery conduit 120. In such an exemplary configuration, the pressure sensor 200 (e.g., the receiving face of the pressure sensor 200) engages a portion of the outer wall of the fluid delivery conduit 120 located within the interior portion of the housing 110 such that pressure within the fluid delivery conduit 120 may exert a force onto the receiving face of the pressure sensor 201. The force exerted on the pressure sensor 200 may be detected by the force transmitting member 250, which may be configured to transmit at least a portion (e.g., all) of the force to the pressure sensing element 220. In various embodiments, the force transmitting member 250 may comprise, for example, a gel.

As described above, the pressure sensing element 220 may be configured to receive high frequency signals (e.g., oscillating signals) emitted by the ultrasonic transmitter 300. The signal emitted by the ultrasonic transmitter 300 is received by the pressure sensing element 220 after traveling through the fluid delivery conduit 120.

In various embodiments, an occlusion within the fluid delivery conduit may result in a change of pressure within the fluid delivery conduit 120, and thus, a change in force being exerted on the inner wall of the fluid delivery conduit 120 and, in turn, a change in force being transmitted from the fluid delivery conduit 120 to the pressure sensor 200. The change in force arising from a change in pressure within the fluid delivery conduit 120 may define a low frequency event received by and transmitted through the force transmitting member 250 such that it may be sensed by the pressure sensing element 220. In various embodiments, a low frequency event experienced by the pressure sensing element 220 may be detected as a shift in signal detected by the pressure sensing element 220 (e.g., correlating to a DC shift). Such a change in the signal to the pressure sensing element 220 may manifest in a proportional DC shift experienced by the pressure sensor's output signal to the controller 140. For example, when the fluid within the fluid delivery conduit 120 experiences occlusion, the resultant change in pressure leads to a change signal voltage output by the pressure sensing element, and thus, a vertical shift of the output signal. Accordingly, in various embodiments, the fluid sensor 10 may be configured to detect occlusion within a fluid delivery conduit 120 by receiving the emitted high frequency signal components from the ultrasonic transmitter 300 and correlating a detected variance in voltage (i.e. DC shifts) in the pressure sensor's resultant output signal to a blockage within the fluid delivery conduit 120.

In various embodiments, to ensure accuracy of the signal detected by the pressure sensing element 220, both the receiving face of the pressure sensor 201 and the emitting face of the ultrasonic transmitter 301 may be positioned at least substantially parallel to and in contact with a portion of the outer wall of the fluid delivery conduit 120 secured within the channel 113. As described above and as shown in FIGS. 3 and 4, the fluid delivery conduit 120 may be compressed in the direction of the conduit's width such that at least substantially all of receiving face of the pressure sensor 201 is in contact with a portion of the outer wall of the fluid delivery conduit 120. Such a configuration enables the entirety of the face of the force transmitting member 250 to be coupled to the surface of the fluid flowing through the fluid delivery conduit 120 for the purposes of sensing force, and prevents any undesirable force "leakage" that is transmitted away from the pressure sensing element 220. In various embodiments, failure to essentially couple the pressure sensing element 220 to the fluid being sensed through the force transmitting member 250, may result in the force transmitting member 250 receiving a distorted signal. Such a distortion may result in the fluid sensor 10 producing inaccurate readings.

Bubble Detection

As described herein, the fluid sensor 10 may be configured to detect the presence of an air bubble 302 within a fluid delivery conduit 120 by detecting a change in the signal (e.g., the oscillating signal component) emitted from the ultrasonic transmitter and received by the pressure sensor 200. For example, the fluid sensor may be configured to detect the presence of an air bubble 302 within a fluid delivery conduit 120 by detecting a change in signal strength at a defined frequency received by the pressure sensor 200. As described above and as shown in FIGS. 3 and 4, the pressure sensor 200 of the fluid sensor 10 may be located within the interior of the housing 110 and arranged such that the receiving face of the pressure sensor 201 is at least substantially parallel to a length of the channel 113 configured to receive and secure at least a portion of the fluid delivery conduit 120. Similarly, the emitting face of the ultrasonic transmitter 301 may be positioned at least substantially parallel to both the receiving face of the pressure sensor 201 and the length of the channel 113 such that the emitting face of the ultrasonic transmitter 301 and the receiving face of the pressure sensor 201 are spaced apart to define a gap 114 configured to accept the fluid delivery conduit 120 therein.

In such an exemplary configuration, the ultrasonic transmitter 300 may be configured to receive a drive signal (e.g., an oscillating drive signal, such as an AC drive signal) from the controller 140 and to emit ultrasonic waves carrying the signal through the emitting face of the ultrasonic transmitter 301, through the portion of the fluid delivery conduit 120 positioned within the gap 114, and to the receiving face of the pressure sensor 201. In various embodiments, wherein the force transmitting member 250 may be, for example, a gel, the gel may act as an incompressible fluid. The emitted signal may be sensed by the pressure sensing element 220, which may be configured to subsequently transmit an output signal to the controller 140 indicative of the detected signal. As described above, the emitted signal may be embodied as an AC signal or another oscillating signal shape, centered on a voltage characterized by a DC shift in the drive signal.

Figure 7:
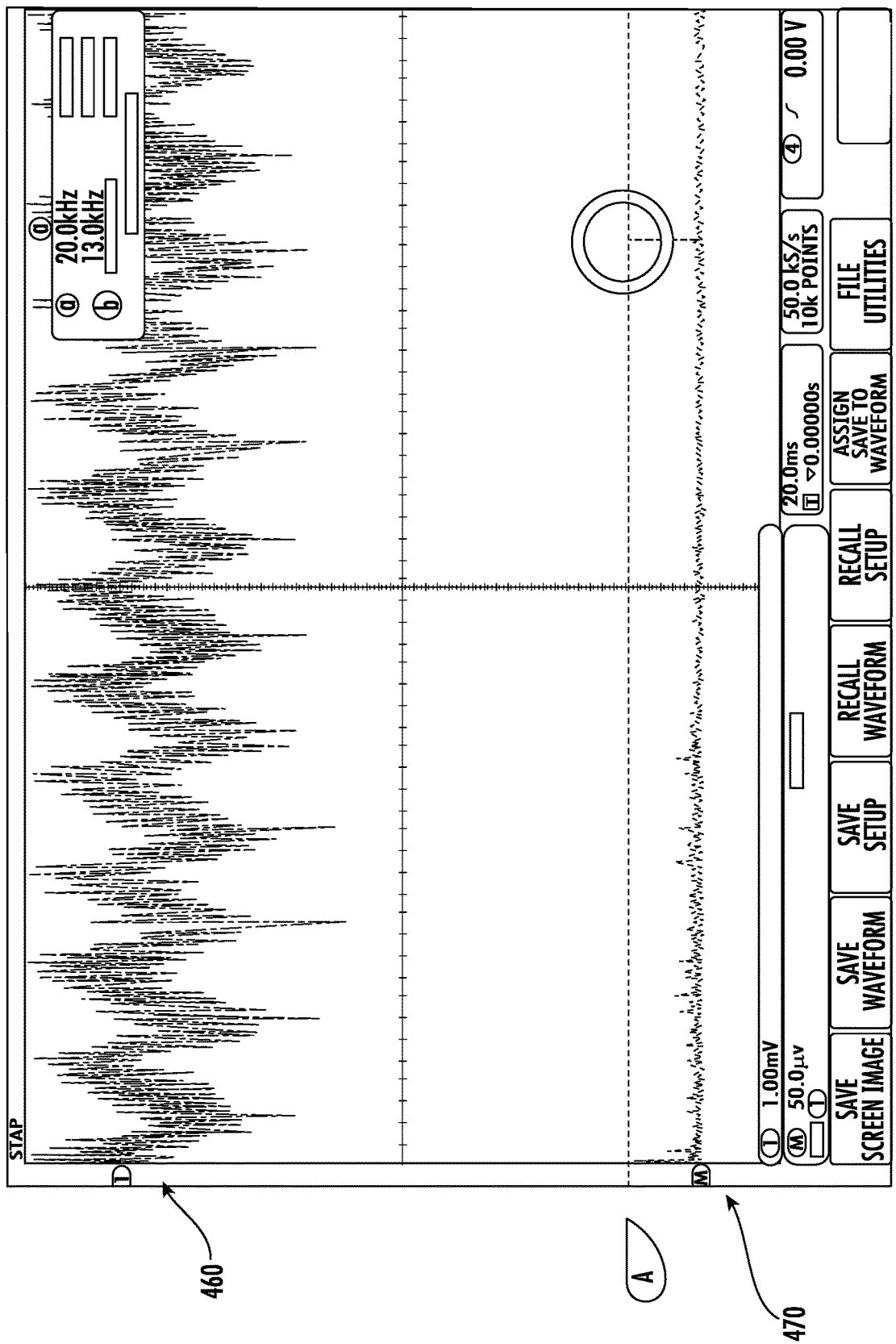
FIG. 7 shows an exemplary graphical representation of signals produced by a testing configuration in accordance with various embodiments.
Figure 8:
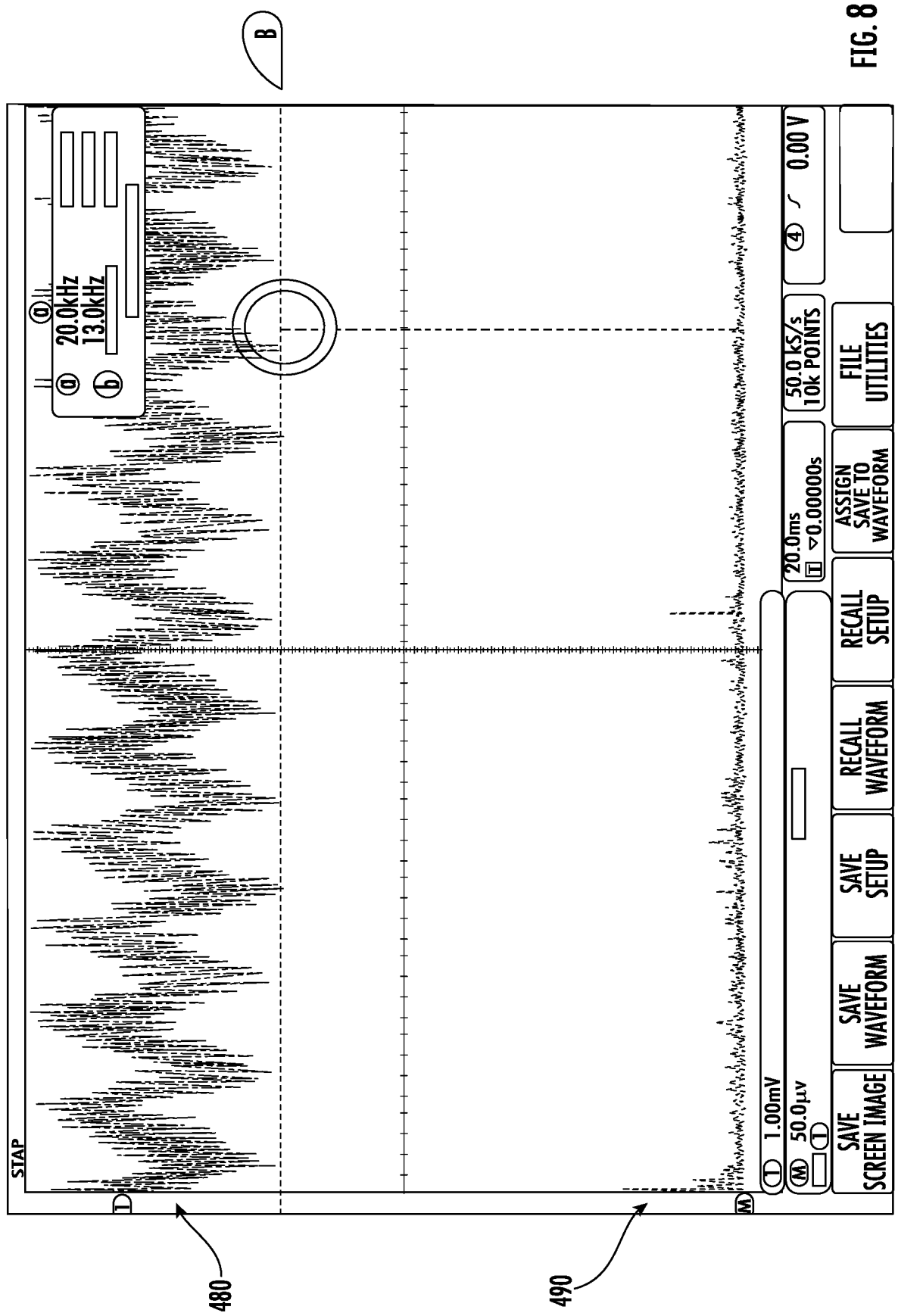
FIG. 8 shows an exemplary graphical representation of signals produced by a testing configuration in accordance with various embodiments.

In an exemplary condition wherein there are no air bubbles present within the fluid delivery conduit 120, as illustrated in FIG. 3, substantially all of the waves emitted from the ultrasonic transmitter 300 are sensed by the pressure sensor 200, resulting in a signal transmitted to the controller 140 that is indicative of an uninterrupted signal transmitted through the fluid delivery conduit 120. Conversely, in an exemplary condition wherein at least one air bubble 302 is present within the fluid delivery conduit 120, as illustrated in FIG. 4, the air bubble 302 may interrupt the direct transmission of the emitted signal from the ultrasonic transmitter 300 to the pressure sensor 200 and may reflect and/or deflect at least a portion of the emitted signal, deflecting the portion of the signal away from the pressure sensing element 220. In such an exemplary circumstance, the reflection of at least a portion of the emitted signal may result in a distorted signal received by the pressure sensing element 220 when represented in the time domain. When the air bubble 302 is present in the fluid delivery conduit 120, the received signal, when presented in a frequency domain, may exhibit, for example, a pronounced signal at the drive frequency of the ultrasonic transmitter 300. Accordingly, in various embodiments, the fluid sensor 10 may be configured to detect the presence of an air bubble 302 within a fluid delivery conduit 120 by monitoring the emitted high frequency signal from the ultrasonic transmitter 300 and correlating a more pronounced signal at the ultrasonic transmitter 300 drive frequency to the presence of a bubble 302 within the fluid delivery conduit 120. Further, in various embodiments, the fluid sensor 10 may be further configured to determine specific characteristics about the detected bubble 302 such as, for example, its size, based on one or more of the distortions in the signal received by the pressure sensing element Signal Analysis As illustrated in FIGS. 7 and 8, in various embodiments a Fast Fourier Transform (FFT) may convert the pressure sensor 200 output signal to transformed data represented in the frequency domain. In various embodiments, the FFT may be performed by either the controller 140 or an external computer in communication with the sensor 10 and configured to perform the FFT. In various embodiments, the transformed data may be indicative of the strength of the pressure sensor output signal across a frequency range. The transformed data in an air-in-tube condition 490 may be discernably different from the transformed data in an air-in-tube condition 470 at one or more frequencies, such as, for example, the ultrasonic transmitter 300 drive frequency. The transformed data in an air-in-tube condition, distinct from that in a fluid-in-tube condition, may comprise a distinguished signal at the frequency along the x-axis correlating to the ultrasonic transmitter 300 drive frequency. In various embodiments, an air-in-tube condition may be detected by comparing the signal-to-noise ratio of the transformed data in an air-in-tube condition to that of the transformed data in a fluid-in-tube condition at the ultrasonic transmitter drive frequency. In various embodiments, a signal contrast ratio of between 2 and 5 (e.g., 3) may be measured when comparing the aforementioned respective transformed data. As described herein, when the fluid sensor 10 detects a signal contrast ratio as described above at the ultrasonic transmitter drive frequency with a value of at least 1 kHz, the controller 140 may be configured to determine that a bubble is present in the fluid delivery conduit 120. Further, in various embodiments, when the fluid sensor 10 detects a signal-to-noise ratio at the ultrasonic transmitter drive frequency of at least between 2 and 5 (e.g., 3), the controller 140 may be configured to determine that a bubble is present in the fluid delivery conduit 120.

In an alternative embodiment, a bandpass filter configured to facilitate bubble detection by isolating one or more signals of interest within a particular band of frequencies. The bandpass filter may be implemented to selectively distinguish the signal at the ultrasonic transmitter drive frequency from the noise present within the signal, thereby producing transformed data to be analyzed without performing a FFT. In various embodiments, the bandpass filter range may be centered at the drive frequency of the ultrasonic transmitter and may be configured to allow a range of frequencies between, for example, within 500 Hz above and/or below the drive frequency to be received (i.e. a 1 kHz band). In various embodiments, when the fluid sensor 10 detects a signal at the ultrasonic transmitter drive frequency, the controller 140 may be configured to determine that a bubble is present in the fluid delivery conduit 120.

Experimental Testing

Experimental testing was conducted to verify the effectiveness of embodiments as described herein. Data was collected over the course of multiple trials using various combinations of embodiments described above.

In the testing configuration, an exemplary fluid sensor used for testing was configured to be in electronic communication with both the pressure sensor controller and the ultrasonic transmitter controller. The pressure sensor controller was configured to transmit a power signal to the pressure sensor. Similarly, the ultrasonic transmitter controller was configured to transmit a power signal to the ultrasonic transmitter. The testing circuitry comprised a drive circuit configured to transmit a signal to the ultrasonic transmitter. The testing circuitry was further electronically connected to an oscilloscope configured to generate the drive signal and graphically display the output signal sensed by the pressure sensor. Example output signals 460, 480 are shown in FIGS. 7 and 8.

Figure 6:
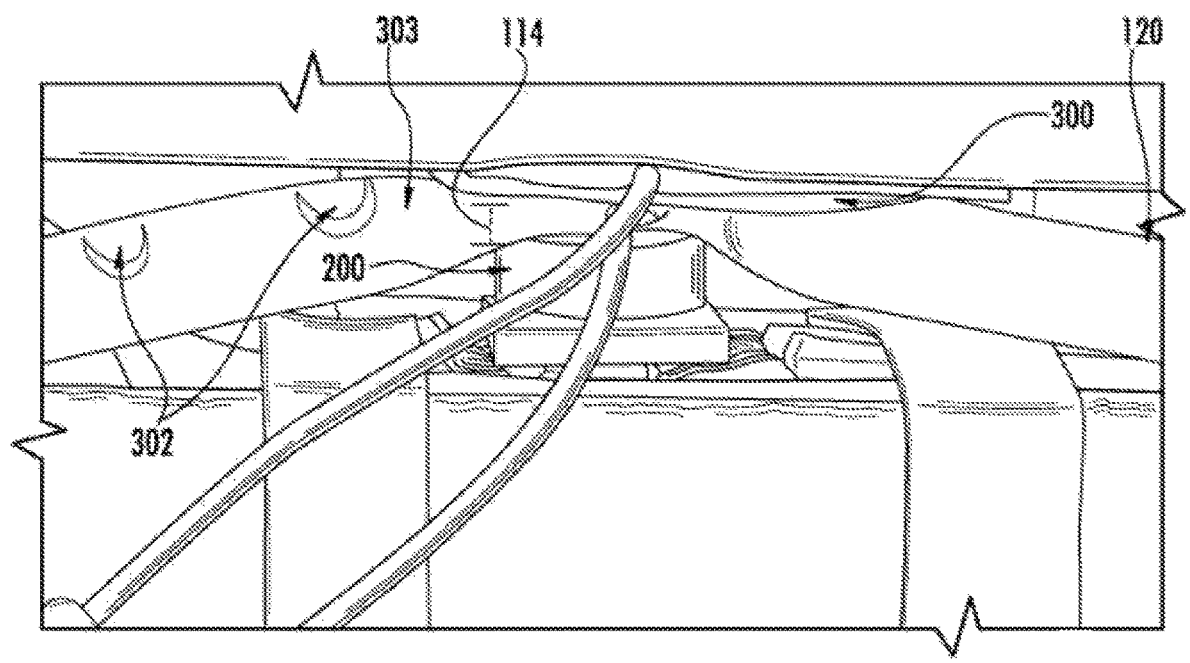
FIG. 6 shows an exemplary test configuration in accordance with various embodiments.

FIG. 6 shows a close-up view of the fluid sensor 10 sensory components used in the exemplary testing configuration. The pressure sensor 200 is secured to the bottom surface of a vise, a configuration meant to recreate the mounting of the pressure sensor 200 within the interior portion of the housing 110. Similarly, the ultrasonic transmitter 300 is secured relative to the top surface of the vise. In such a configuration, the pressure sensor 200 and the ultrasonic transmitter 300 are spaced apart so as to define a gap 114 configured to receive a portion of the fluid delivery conduit 120. As shown in FIG. 6, the testing configuration comprised the pressure sensor 200 and the ultrasonic transmitter 300 mounted to a vise so as to replicate the requisite compression applied to the fluid delivery conduit 120 when secured within the housing 100 of the fluid sensor 10. As described above, the fluid delivery conduit 120 was compressed by the vise such that the entirety of the receiving face of the pressure sensor 201 was covered by at least a portion of the outer wall of the fluid delivery conduit 120. The exemplary testing configuration utilized a fluid 303 flowing through the tube with deliberately injected air bubbles 302 present within the fluid delivery conduit 120 to enable analysis of the signal sensed by the pressure sensor 200 under conditions both with and without air bubbles 302 present within the fluid delivery conduit 120.

FIG. 7 shows a graphical representation of an example pressure sensor output signal 460 represented in the time domain and example transformed data 470, both under baseline fluid conditions. As described above, the characteristics of the corresponding ultrasonic transmitter drive signal may be selected to produce a drive signal shape for use in conjunction with the specific testing circuitry. Here, the shape of the example ultrasonic transmitter drive signal is similar to that of a general sinusoidal AC signal. As illustrated in FIGS. 7 and 8, the ultrasonic transmitter drive signal has a frequency selected to be above the normal hearing range of humans. For example, the drive frequency may be 20 kHz, although it should be understood that other frequencies may be utilized. The shape of the example pressure sensor output signal 460, 480—shown in FIGS. 1 and 8—may vary from that shown therein, and generally correlates to a baseline fluid pressure within a fluid delivery conduit void of air bubbles. The example pressure sensor output signal 460 is centered around an axis which may represent a signal shift of, for example, 300 mV. Upon detection of a change in pressure, the pressure sensor output signal 460 may shift vertically to represent the change in pressure. A DC shift of the pressure sensor output signal 460 may correspond to a change in pressure within the fluid delivery conduit 120 due to, for example, occlusion.

FIG. 7 further illustrates the resultant transformed data 470 after a FFT has been performed on the pressure sensor output signal 460. Like the pressure sensor output signal 460, the transformed data 470 is representative of a fluid-in-tube condition. As shown, an 98 µV signal, highlighted by exemplary axis A for reference, was measured at the 20 kHz ultrasonic transmitter drive frequency.

FIG. 8 shows an exemplary distorted pressure sensor output signal wave sensed by the pressure sensor 480 and example transformed data, both distorted by the presence of a gas bubble within a fluid delivery conduit 120. As described above, in a condition in which gas bubbles 302 are present within the fluid delivery conduit 120, the output signal 480 may exhibit characteristics different from those of the output signal under normal baseline fluid conditions 460. However, depending on, for example, the input signal characteristics, such differences may be hard to detect in various embodiments. Accordingly, as illustrated by the resultant air-in-tube transformed data 490 in FIG. 8, a FFT was performed on the pressure sensor output signal 480 to represent the signal in the frequency domain. As shown in FIG. 8, a 308 µN signal, highlighted by exemplary axis B for reference, was measured at the 20 kHz ultrasonic transmitter drive frequency. Notably, the signal measured at the 20 kHz ultrasonic transmitter drive frequency during an air-in-tube condition was significantly greater than the corresponding signal measured at the same frequency during a fluid-in-tube condition. In the exemplary test configuration described herein, the signal contrast ratio between the signal air-in-tube transformed data 490 (308 µV) and the signal fluid-in-tube transformed data 470 (98 µV) at 20 kHz was approximately 3:1. In various embodiments, such transformed data comprising such an exemplary strong signal strength at the ultrasonic transmitter drive frequency may indicate the presence of bubble within the fluid delivery conduit 120. In various exemplary testing embodiments, a signal contrast ratio of, for example, approximately between 2 and 5 may be indicative of the presence of a bubble within the fluid delivery conduit 120.

As described herein, the fluid sensor 10 is configured so as to enable the simultaneous monitoring of both the AC and DC components of the pressure sensor output signal. Critically, such a configuration may effectively reduce the error rate of the sensor by compensating for unwarranted external forces that may affect the sensor's acoustic baseline and lead in inaccuracies. Such a shift of the sensor's acoustic baseline may be caused by factors such as, for example, tubing/plastic deformation, temperature change, and/or fluid pressure that result in an unwarranted change of contact force to the sensor. Configuring the components of the fluid sensor in such a way that enables the coupling of the AC and DC components enables the efficient and accurate characterization of flow within a fluid delivery conduit.

CONCLUSION

Many modifications and other embodiments will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A fluid sensor, the fluid sensor comprising:
an ultrasonic transmitter configured to emit ultrasonic signals;
a pressure sensor configured to detect pressure changes, to receive the ultrasonic signals from the ultrasonic transmitter, and to generate a pressure sensor output signal based on the detected pressure changes and the received ultrasonic signals; and
a controller configured to detect a presence of at least one bubble flowing through a fluid delivery conduit based at least in part on a frequency based analysis of the pressure sensor output signal.

2. The fluid sensor of claim 1, wherein the ultrasonic transmitter is configured to emit the ultrasonic signals through an emitting face and the pressure sensor receives the ultrasonic signals through a receiving face.

3. The fluid sensor of claim 2, wherein the emitting face of the ultrasonic transmitter is spaced apart from the receiving face of the pressure sensor to collectively define a gap configured to receive the fluid delivery conduit.

4. The fluid sensor of claim 3, further comprising a housing, wherein the housing comprises an exterior housing portion and an interior housing portion, and wherein the ultrasonic transmitter and the pressure sensor are enclosed within the interior housing portion.

5. The fluid sensor of claim 4, wherein the interior housing portion further defines a channel configured to secure at least a portion of the fluid delivery conduit within the interior housing portion and wherein at least a portion of the channel is aligned with the gap.

6. The fluid sensor of claim 3, wherein at least a portion of the fluid delivery conduit positioned within the gap is compressed such that at least substantially all of the receiving face of the pressure sensor is engaged by at least the portion of the fluid delivery conduit.

7. The fluid sensor of claim 1, wherein the pressure sensor comprises:
a pressure sensing element mounted to a substrate; and a force transmitting member positioned adjacent to the pressure sensing element, wherein the force transmitting member transmits a force applied to a front side of the force transmitting member to a front side of the pressure sensing element.

8. The fluid sensor of claim 7, wherein the force transmitting member is a gel.

9. The fluid sensor of claim 1, wherein the controller is configured for wireless communication of an output signal.

10. The fluid sensor of claim 1, wherein the ultrasonic transmitter is configured to receive a drive signal from the controller, wherein the drive signal comprises at least one of an AC component or a DC component.

11. The fluid sensor of claim 1, wherein the ultrasonic transmitter comprises a piezoelectric ultrasonic transducer.

12. The fluid sensor of claim 1, wherein the fluid sensor is configured to detect the pressure changes within the fluid delivery conduit based at least in part on a detected shift in the received ultrasonic.

13. The fluid sensor of claim 1, wherein the controller is configured to construct transformed data by performing a Fast Fourier Transform of the pressure sensor output signal, and wherein the transformed data is indicative of a strength of the pressure sensor output signal across a frequency range.

14. The fluid sensor of claim 13, wherein the fluid sensor is configured to detect the presence of the at least one bubble flowing through the fluid delivery conduit by measuring a detected change in the transformed data at a frequency that is at least substantially similar to a drive frequency of the ultrasonic transmitter.

15. A method of detecting at least one air bubble within a fluid delivery conduit of a fluid sensor, the method comprising:
receiving a received signal from an ultrasonic transmitter at a pressure sensor, the pressure sensor being configured to detect pressure changes and generate a pressure sensor output signal based at least in part on the received signal and the detected pressure changes; and
detecting the at least one air bubble within the fluid delivery conduit based at least in part on a frequency based analysis of the pressure sensor output signal.

16. The method of claim 15, further comprising emitting the received signal as ultrasonic signals from the ultrasonic transmitter, through the fluid delivery conduit, and to the pressure sensor aligned with the ultrasonic transmitter on an opposite side of the fluid delivery conduit, the pressure sensor configured to receive the ultrasonic signals emitted from the ultrasonic transmitter.

17. The method of claim 15, wherein a DC shift in the pressure sensor output signal corresponds to the pressure changes within the fluid delivery conduit.

18. The method of claim 15, wherein a controller is configured to construct transformed data by performing a Fast Fourier Transform of the pressure sensor output signal, and wherein the transformed data is indicative of a strength of the pressure sensor output signal across a frequency range.

19. The method of claim 18, wherein detecting the at least one air bubble within the fluid delivery conduit comprises:
measuring a detected change in the transformed data at a frequency that is at least substantially similar to a drive frequency of the ultrasonic transmitter.

20. The method of claim 19, wherein the fluid sensor comprises a bandpass filter centered at the drive frequency of the ultrasonic transmitter to selectively distinguish the pressure sensor output signal at the drive frequency of the ultrasonic transmitter from noise present within the pressure sensor output signal.

* * * * *